US008865414B2

(12) United States Patent
Hennig et al.

(10) Patent No.: US 8,865,414 B2
(45) Date of Patent: Oct. 21, 2014

(54) DETECTION CONJUGATE AND METHOD FOR ANALYSIS

(75) Inventors: Christian Hennig, Hannover (DE); Gesine Hansen, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 566 days.

(21) Appl. No.: 13/139,870

(22) PCT Filed: Dec. 17, 2009

(86) PCT No.: PCT/EP2009/067384
§ 371 (c)(1),
(2), (4) Date: Sep. 6, 2011

(87) PCT Pub. No.: WO2010/070037
PCT Pub. Date: Jun. 24, 2010

(65) Prior Publication Data
US 2011/0311966 A1    Dec. 22, 2011

(30) Foreign Application Priority Data

Dec. 17, 2008 (DE) .................. 10 2008 062 372

(51) Int. Cl.
*G01N 33/53* (2006.01)
*C07K 14/00* (2006.01)
*C07K 16/00* (2006.01)
*C12Q 1/68* (2006.01)
*C07H 21/00* (2006.01)
*C07H 21/02* (2006.01)
*C07H 21/04* (2006.01)

(52) U.S. Cl.
CPC ................... *C12Q 1/6804* (2013.01)
USPC .......... 435/7.1; 530/350; 530/387.1; 435/6.1; 536/22.1; 536/23.1; 536/24.3

(58) Field of Classification Search
USPC ................. 435/6.1, 7.1; 536/22.1, 23.1, 24.3; 530/350, 387.1
See application file for complete search history.

(56) References Cited

U.S. PATENT DOCUMENTS

| | | | | |
|---|---|---|---|---|
| 5,561,043 A * | 10/1996 | Cantor et al. | ................. | 435/6.16 |
| 5,718,915 A * | 2/1998 | Virtanen et al. | ............... | 424/450 |
| 5,733,523 A * | 3/1998 | Kuijpers et al. | ............... | 424/1.73 |
| 5,925,517 A * | 7/1999 | Tyagi et al. | ..................... | 435/6.1 |
| 5,942,391 A * | 8/1999 | Zhang et al. | .................. | 435/6.12 |
| 6,143,495 A * | 11/2000 | Lizardi et al. | ................. | 435/6.12 |
| 6,150,173 A | 11/2000 | Schubert | | |
| 6,350,580 B1 * | 2/2002 | Sorge | ......................... | 435/6.11 |
| 6,511,809 B2 * | 1/2003 | Baez et al. | .................... | 435/6.11 |
| 7,129,048 B2 * | 10/2006 | Bruchez et al. | ................ | 435/6.14 |
| 7,229,763 B2 * | 6/2007 | Reddy et al. | .................. | 435/6.16 |
| 7,910,294 B2 * | 3/2011 | Karlsen | ........................ | 435/6.14 |
| 8,309,306 B2 * | 11/2012 | Nolan et al. | ................... | 435/6.1 |
| 2001/0009760 A1 * | 7/2001 | Horn et al. | ....................... | 435/6 |
| 2004/0106553 A1 * | 6/2004 | Alekshun et al. | ............... | 514/12 |
| 2004/0219526 A1 | 11/2004 | Reddy et al. | | |
| 2005/0287548 A1 * | 12/2005 | Bao et al. | ......................... | 435/6 |
| 2007/0224128 A1 * | 9/2007 | Dennis et al. | ................ | 424/10.1 |
| 2008/0124705 A1 * | 5/2008 | Kramer | .............. | 435/6 |
| 2010/0015622 A1 * | 1/2010 | Hanna et al. | ..................... | 435/6 |
| 2010/0041049 A1 * | 2/2010 | Smith et al. | ...................... | 435/6 |
| 2010/0227850 A1 * | 9/2010 | Alekshun et al. | ......... | 514/211.11 |
| 2011/0287557 A1 * | 11/2011 | Zhang et al. | .................. | 436/501 |

FOREIGN PATENT DOCUMENTS

| WO | WO 2004/057023 | 7/2004 |
|---|---|---|
| WO | WO 2006/002167 | 1/2006 |
| WO | WO 2007/101706 | 9/2007 |

OTHER PUBLICATIONS

Chen et al., DNA hybridization detection in a microfluidic channel using two fluorescently labelled nucleic acid probes. Biosensors and Bioelectronics 23 :1878 (Mar. 2008).*
Jayasena, S.D.Aptamers: An Emerging Class of Molecules That Rival Antibodies in Diagnostics. Clinical Chemistry 45(9) :1628 (1999).*
Lichlyter et al.,Development of a novel FRET immunosensor technique. Biosensors and Bioelectronics 19 :219 (2003).*
Oh et al., Chimeric peptide beacons: a direct polypeptide analog of DNA molecular beacons. Chemical Communications Oct. 2007 p. 4869.*
Shamansky et al. Immobilization and detection of DNA on microfluidic chips. Talanta 55 :909 (2001).*
Stojanovic et al., Aptamer-Based Folding Fluorescent Sensor for Cocaine JACS 123 : 4928 (2001).*
Wei et al. Bifluorophoric molecules as fluorescent beacons for antibody-antigen binding. Journal of Molecular recognition 15 :311 (2002).*
Chen et al., A new method for the detection of ATP using a quantum-dot-tagged aptamer. Analytical and Bioanalytical Chemistry 392:1185 (Oct. 2008)].*
Hennig, Christian et al.. "A Versatile Platform for Comprehensive Chip-Based Explorative Cytometry," *International Society of Advancement of Cytometry*, 75A: pp. 362-370, 2009.
Mittag, Anja et al., "Hyperchromatic Cytometry Principles for Cytomics Using Slide Based Cytometry," *International Society for Analytical Cytology*, Cytometry Part A 69A: pp. 691-703, 2006.
Tárnok, Attila, Slide-Based Cytometry for Cytomics—A Minireview, *International Society for Analytical Cytology*, Cytometry Part A 69A: 555-562, 2006.

(Continued)

*Primary Examiner* — Ethan C Whisenant
(74) *Attorney, Agent, or Firm* — Greer, Burns & Crain, Ltd.

(57) ABSTRACT

The invention provides a combination of reagents as a test kit containing a detection conjugate having a binding portion and a reagent for deactivating of the fluorochrome portion by interaction with the linker. The binding portion especially is an antibody portion. The detection conjugate has a fluorochrome portion connected to the antibody portion, and a linker connected to the fluorochrome portion, wherein the linker comprises an oligonucleotide. The fluorochrome portion can be deactivated by hydrolysis of the linker or by specific hybridization of a quencher having an oligonucleotide to the linker.

29 Claims, 6 Drawing Sheets

(56) References Cited

OTHER PUBLICATIONS

Figure 1:
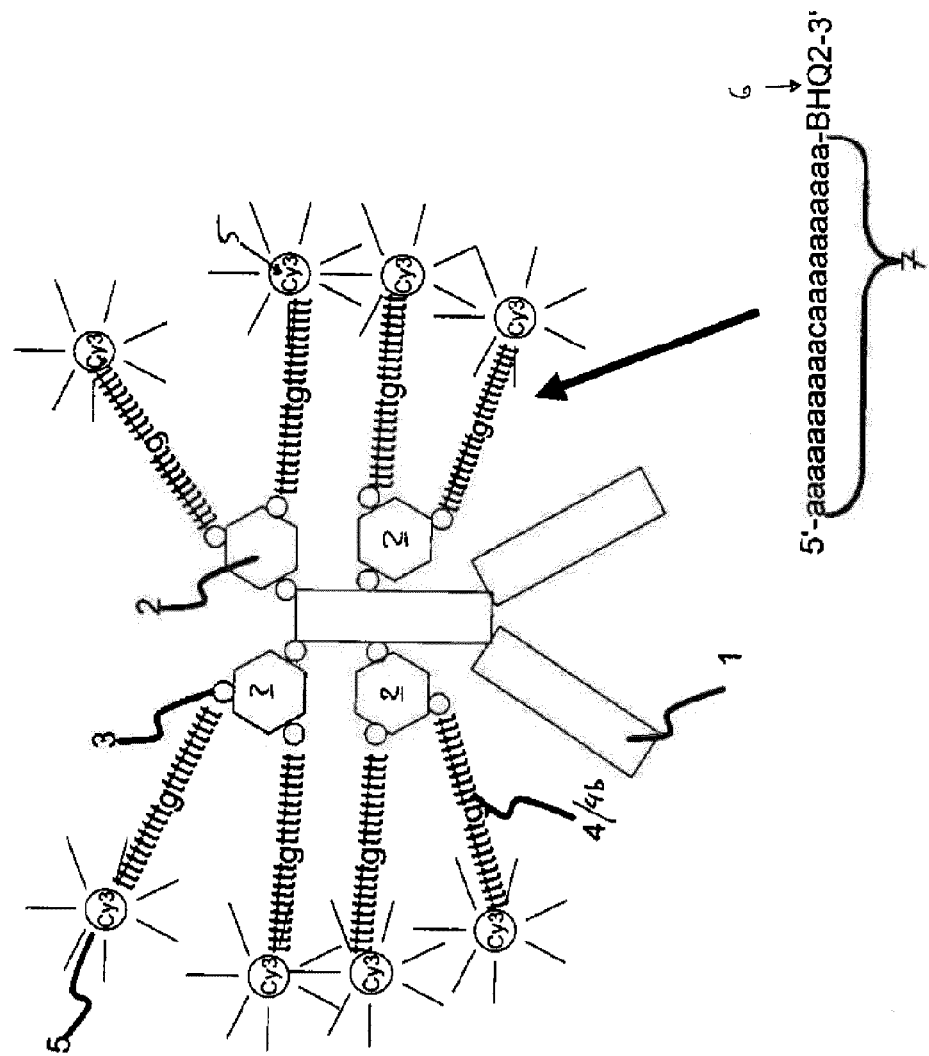

Mittag, Anja et al., "Sequential Photobleaching of Fluorochromes for Polychromatic Slide-Based Cytometry," *International Society for Analytical Cytology*, Cytometry Part A 69A: pp. 139-141, 2006.

Mahnke, Yolanda et al., Optimizing a Multi-colour Immunophenotyping Assay, *Clin Lab Med*. 37(3): 469-v, 2007.

Laffers, Wiebke et al., "Iterative Restaining as a pivotal Tool for n-Color Immunophenotyping by Slide-Based Cytometry," *International Society for Analytical Cytology*, Cytometry Part A 69A: pp. 27-130, 2006.

Perfetto, Stphen P. et al., "Seventeen-colour flow cytometry: unraveling the immune system," *Nature Reviews*, vol. 4, pp. 648-655, Aug. 2004.

* cited by examiner

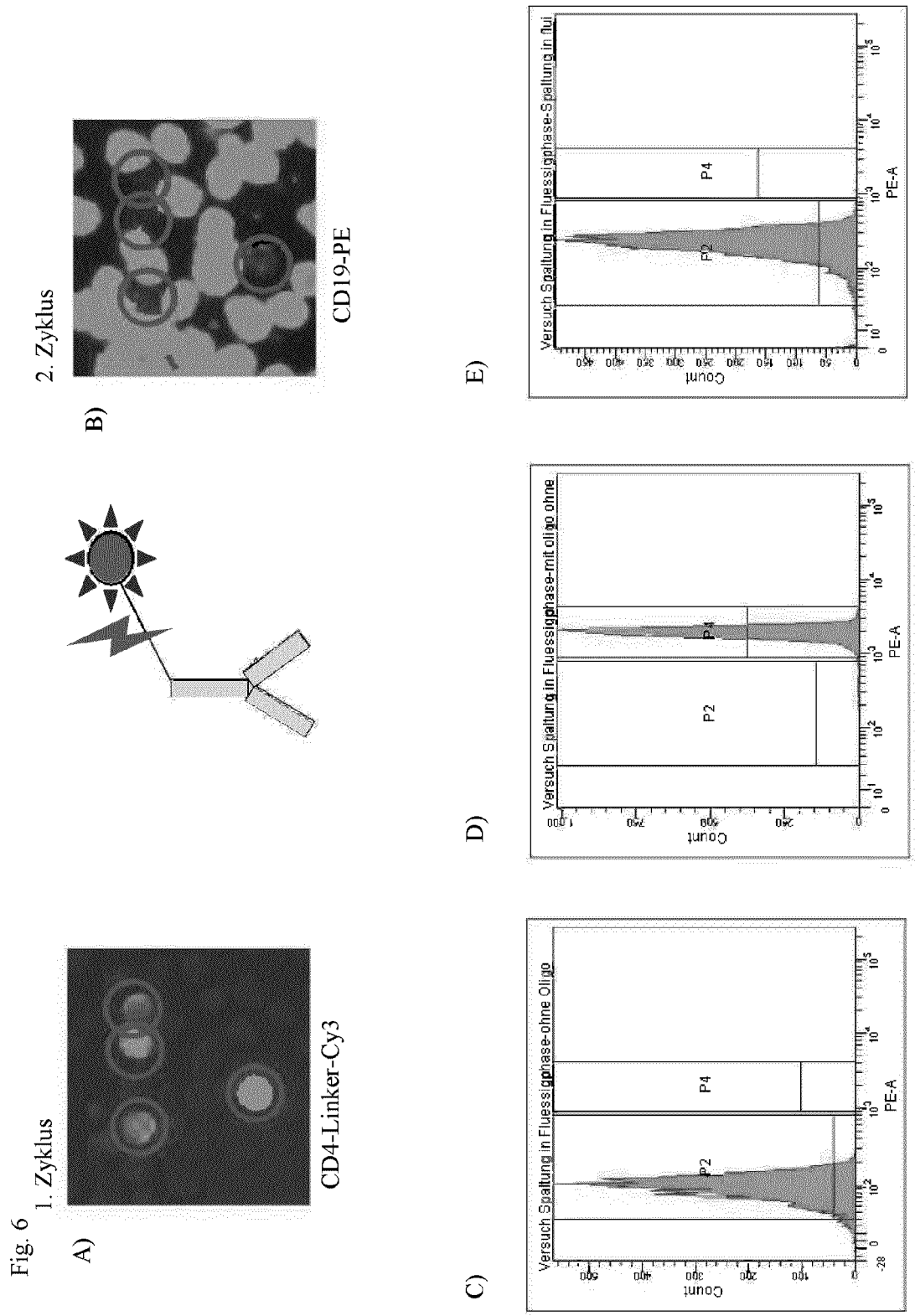

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: /note="oligonukleotide linker, SEQ ID NO: 1"

<400> SEQUENCE: 1
tttttttttt gtttttttt                                                   20

<210> SEQ ID NO 2
<211> LENGTH: 21
<212> TYPE: DNA
<213> ORGANISM: Artificial
<220> FEATURE:
<223> OTHER INFORMATION: /note="hybridising oligonukleotide, SEQ ID NO:
      2"

<400> SEQUENCE: 2
aaaaaaaaaa caaaaaaaaa a                                                21

<210> SEQ ID NO 3
<211> LENGTH: 25
<212> TYPE: DNA
<213> ORGANISM: Artificial Sequence
<220> FEATURE:
<223> OTHER INFORMATION: /note="synthetic aptamer, SEQ ID NO:. 3"

<400> SEQUENCE: 3
gcagttgatc ctttggatac cctgg                                            25

<210> SEQ ID NO 4
<211> LENGTH: 33
<212> TYPE: DNA
<213> ORGANISM: Artificial Sequence
<220> FEATURE:
<223> OTHER INFORMATION: /note="synthetic aptamer, SEQ ID NO: 4"
```

```
<400> SEQUENCE: 4
ucguaugggu gggaucggga agggcuacga aca                    33
```

DETECTION CONJUGATE AND METHOD FOR ANALYSIS

The invention relates to detection conjugates having an antibody portion, methods for detection of analytes using a detection conjugate, and to the use of the detection conjugates in methods for specific detection of analytes, e.g. of specific antigens which are in solution, extracellularly or intracellularly bound to suspended cells or to cells bound to a carrier substrate or which antigens are bound to a carrier substrate, and particularly are arranged at living cells or at denatured and permeabilized cells, which are in suspension or bound to a carrier substrate. As an alternative to the antibody portion detection conjugates contain a binding portion specific for an analyte, e.g. a receptor ligand, a receptor, a specifically binding molecule, e.g. a lectin, biotin, avidin, an oligosaccharide, each as binding portion of the detection conjugate.

Detection conjugates according to the invention comprise a binding portion and a fluorochrome portion connected thereto, which is connected to a first end of a linker. The binding portion can be arranged at the second end of the linker opposite the first end, such that the linker is arranged between the binding portion and the fluorochrome portion. The detection conjugates are characterized in that the linker bound to the fluorochrome portion of the conjugate is disposed to deactivate the optical activity of the fluorochrome portion of the conjugate by interaction with a reagent. In a first embodiment the binding portion can be connected to the fluorochrome portion, whereas the linker with its first end is connected to the fluorochrome portion.

The disposition of the linker according to the invention to deactivate the optical activity of the fluorochrome portion in presence of a reagent which is a compound specifically reactive with the linker allows detection methods in which at least two detection conjugates having differing specificities are used simultaneously and/or successively, each time including the step of linker-specific deactivation of the optical activity of the fluorochrome portion in the conjugate, e.g. after detection of a detection conjugate, such that e.g. in use in the alternative to bleaching no mutual disturbance occurs for identical or differing fluorochrome portions of the conjugates, for example interference or the mutual excitation of fluorochromes do not happen. In this manner, a nonspecific reduction of the optical signal from a fluorochrome or the generation of a nonspecific optical signal from a conjugate are avoided which remains from a previous step of analysis. Preferably, the linkers of conjugates which are contacted with the same sample successively or concurrently have differing binding specificities for a matching specific reagent for deactivating the fluorochrome portion each.

STATE OF THE ART

Mahnke and Roederer (Clin. Lab. Med. 2007, 27(3) (2007)) describe how a majority of antibody conjugates can be coordinated to each other for the detection of antigens on cells in flow cytometry in order to avoid interferences of the fluorochrome portions upon simultaneous use, which fluorochrome portions have different emission spectra each in order to be distinguishable. For separation of overlapping emission spectra, particularly upon nonspecific excitation of a fluorochrome by energy transfer from another fluorochrome, a computer-aided evaluation of the signals is proposed in which nonspecific emission signals can be detracted as background.

Laffers et al. (Cytometry Part A 69A: 127-130 (2006)) describe the analysis of cells by flow cytometry or of immobilized cells with antibody-fluorochrome conjugates having different fluorochromes each. For evaluation the data from flow cytometry (FC) or microscopy using fluorescence detection were superimposed in a computer-aided way.

Tárnok (Cytometry Part A 69 A:555-562 (2006)) in addition to cytometry using antibody conjugates with different fluorochromes mentions the successive application of antibody-fluorochrome conjugates, the bleaching of fluorochromes by irradiation, the activation and the destruction of fluorochromes by radiation.

Perfetto et al. (Nature 648-654 (2004)) describe flow cytometers for the detection of a multitude of fluorochromes by specific excitation and wavelength-specific detection of emitted light each in rapid succession, which is called simultaneous measuring. It is shown that different fluorochromes which are concurrently present in a sample nonetheless show nonspecific emissions upon excitation with a wavelength which is fluorochrome-specific, which is attributed to an energy transfer between the fluorochromes. For avoidance of nonspecific signals there is proposed the coordination of the concurrently utilized antibody-fluorochrome conjugates in an empirical method. For further reduction of nonspecific emission signals a mathematical compensation is proposed with which emissions are substracted which can be traced back to the nonspecific energy transfer between fluorochromes.

U.S. Pat. No. 6,150,173 describes a computer-controlled pipetting automat by which antibody-fluorochrome conjugates are successively incubated with a sample, the emitted radiation is measured after irradiation with an excitation wavelength, subsequently the fluorochrome is destructed by irradiation with UV, and a new antibody-fluorochrome conjugate is added to the same sample.

WO 2007/101706 A1 describes that prior to the detection of a specific antibody-fluorochrome conjugate the biological sample is treated by irradiation in order to reduce nonspecific fluorescence.

In the afore-mentioned methods for detection of several antibody-fluorochrome conjugates it is disadvantageous that fluorochromes can emit light nonspecifically, for example after energy transfer from another fluorochrome, if several different fluorochromes are used simultaneously for the analysis of a sample. It is disadvantageous in methods in which antibody-fluorochrome conjugates are successively contacted with a sample, wherein each time one fluorochrome is destructed by irradiation, that on the one hand a high energy input for destruction of fluorochromes can change the sample, and on the other hand the destruction of a fluorochrome does not take place completely and not irreversibly, respectively, such that even after such a destructive irradiation nonspecific emissions of fluorochromes can often be detected which is also called regeneration of the fluorochromes.

Furthermore, the relatively long duration of irradiation is disadvantageous in methods for deactivating fluorochromes by irradiation.

OBJECT OF THE INVENTION

In view of the known state of the art, it is an object of the invention to provide reagents having a conjugate having a binding portion specifically binding an analyte and a fluorochrome portion (also called fluorophore or fluorescence dye) with which the disadvantages of the state of the art are avoided, especially to provide a binding portion-fluorochrome conjugate, particularly an antibody-fluorochrome conjugate which is disposed such that upon simultaneous and/or sequential contacting of a sample with at least two binding portion—fluorochrome portion conjugates the effect of a fluorochrome is selectively deactivateable.

Furthermore it is an object of the invention to provide a method for analysis using the reagents, in which method the optical activity of at least one fluorochrome is deactivated between the contacting of the sample with different binding portion—fluorochrome conjugates, particularly for conjugates having different binding portions and identical fluorochrome portions. It is aspired that the analytical method substitutes the irradiation for deactivating of fluorochromes by a selective interaction of a reagent with the fluorochrome.

GENERAL DESCRIPTION OF THE INVENTION

The invention achieves the afore-mentioned objects with the features of the claims and particularly provides a combination of reagents, which is also called a test kit, which contains a detection conjugate having a binding portion and a reagent for deactivating the fluorochrome portion by interaction with the linker. The binding portion in particular is an antibody portion. The detection conjugate has a fluorochrome portion connected to the antibody portion and a linker connected to the fluorochrome portion, wherein the linker comprises or consists of an oligonucleotide. Preferably, the linker with its first end is connected to the fluorochrome portion. Optionally, the linker with its second end opposite the first end is connected to the binding portion, such that the linker connects the binding portion and the fluorochrome portion to one another. Since the linker comprises an oligonucleotide or consists thereof the linker is also termed oligonucleotide linker. The detection conjugate can consist of the binding portion, which preferably is a natural or synthetic antibody, of the fluorochrome and of the oligonucleotide linker. For the purposes of the invention the term oligonucleotide generally comprises single-stranded and double-stranded DNA and/or RNA and synthetic oligonucleotide sequences, for example PNA (peptide nucleic acid), especially having a length in the range of 6 to 200 nucleotides, preferably 20 to 100 nucleotides.

For the following description the term antibody is used to represent a binding portion and the term detection conjugate or antibody conjugate is also used to represent binding portion conjugates having another binding portion in the place of the antibody portion which binding portion e.g. is selected from the group which consists of oligonucleic acids, receptor ligands, receptors, lectins, oligosaccharides, coordinative complexes, antigens, e.g. aptamers, peptides which are specific for a predetermined MHC I or MHC II, MHC-tetramers, biotin, avidin, and paratope forming antibody fragments. A binding portion has an affinity to an analyte which is a binding partner to the binding portion. As binding portion of high affinity antibodies and their paratope forming sections are preferred, as well as aptamers. An aptamer which is a binding portion preferably consists of single-stranded DNA or RNA, e.g. with or of the sequence 5'-GCAGTTGATCCTTTG-GATACCCTGG-3' (SEQ ID NO: 3) which is specific for the tumor marker MUC1 S1.3 or 5'-UCGUAUGGGUGG-GAUCGGGAAGGGCUACGAACA-3' (SEQ ID NO: 4) which is specific for the mouse-CD30 (lymphoma marker).

In a first embodiment the combination of reagents in addition to the first reagent containing the detection conjugate as second reagent, which deactivates the fluorochrome portion of the detection conjugate upon contacting, contains a quencher connected to an oligonucleotide specifically hybridizeable with the oligonucleotide of the oligonucleotide linker and which oligonucleotide especially has a section having a base sequence reverse complementary to the oligonucleotide linker. Preferably, the oligonucleotide of the quencher has a length sufficient for hybridizing to the oligonucleotide linker, e.g. a length of 10 to 30 nt. The section of the oligonucleotide linker to which the oligonucleotide connected to the quencher is hybridizeable is also termed quencher section.

Preferably, the oligonucleotide linker connects the binding portion to the fluorochrome portion, however, in the alternative, the oligonucleotide linker can be bound only to the fluorochrome portion, and the fluorochrome portion can be connected to the binding portion directly or by means of a binding group. This is because also in this arrangement the effect according to the invention occurs of the oligonucleotide linker providing in the detection conjugate a nucleotide sequence as a quencher section to which a hybridizeable oligonucleotide with a bound quencher binds, such that the quencher is arranged in the proximity to the fluorochrome portion.

In the first embodiment the oligonucleotide contained as a component of the oligonucleotide linker in the antibody conjugate according to the invention allows the specific deactivation of the fluorochrome, since the oligonucleotide bound to the quencher arranges the quencher to the fluorochrome portion by hybridizing with the quencher section of the oligonucleotide linker, and the quencher consequently receives radiation emitted by the fluorochrome portion.

In the first embodiment the antibody conjugate according to the invention is suitable for a test kit and a detection method having at least two detection conjugates utilized in succession, since the fluorochrome portion can be deactivated by the quencher being coordinated in an immediate spatial proximity to the fluorochrome portion, which quencher is capable of receiving and radiationless extinguishing radiation emitted by the fluorochrome portion. In each embodiment and variant of the invention optionally at least two, preferably 2 to 10 or up to 4 antibody conjugates can be used simultaneously in the place of an antibody conjugate. The disposition of the antibody conjugate coordinating a quencher to the fluorochrome portion of a conjugate is realized in that the quencher is provided with an oligonucleotide hybridizeable to a quencher section of the oligonucleotide linker, especially having a base sequence reverse complementary to a quencher section of the oligonucleotide linker. For example the oligonucleotide connected to the quencher can be an antisense-oligonucleotide hybridizeable to the quencher section of the oligonucleotide linker, e.g. RNA, DNA or PNA, preferably an oligonucleotide which in aqueous solution hybridizes to a section of the oligonucleotide linker, which is adjacent to the fluorochrome portion. It has been found that the hybridization of an oligonucleotide connected to a quencher, which oligonucleotide is reverse complementary to a quencher section of the oligonucleotide linker brings this quencher into a confined spatial proximity to the fluorochrome portion of the conjugate, such that the fluorochrome portion and the quencher lie within the Förster radius and the energy transfer occurs from the fluorochrome portion to the quencher, and from this occurs the radiationless and optically not detectable dissipation of energy.

In a second embodiment the oligonucleotide linker is arranged between the binding portion and the fluorochrome portion and the deactivation of the fluorochrome is achieved upon use in analytical methods by hydrolysis of the linker, so that independently from the binding of the antibody to an antigen the fluorochrome portion of the conjugate is separated and is thereby deactivated for the site-specific detection, e.g. for emission of radiation at the binding place of the binding portion. For hydrolysis of the oligonucleotide linker according to the invention nonspecific hydrolases, for example ribonucleases (RNases), deoxyribonucleases (DNases), especially endo-RNases and endo-DNases are used, as well as the specific restrictase, if the oligonucleotide linker contains a nucleotide sequence specific for a restrictase.

The oligonucleotide linker of binding portion conjugates according to the invention can generally be bound to the binding portion covalently or by means of coupling groups, e.g. by a thio, ester, amide or amine bond and by an at least bifunctional compound covalently or by means of a complex of two coupling groups specifically binding to one another, especially complex forming coupling groups, one of which is connected to the binding portion and one is connected to the oligonucleotide linker or covalently bound. In this way, biotin and avidin, or biotin and streptavidin can be coupling groups, one group of which is connected to one end of the oligonucleotide linker and the other one is connected to the binding portion and/or to the fluorochrome portion.

One of the binding possibilities of the oligonucleotide linker to the binding portion can be used in each embodiment for binding of the fluorochrome portion to the oligonucleotide linker and, independently therefrom, in the first embodiment for binding of the quencher to its oligonucleotide.

The deactivation of the fluorochrome portion of an antibody-fluorochrome conjugate according to the invention each time allows successive detection reactions of different epitopes or antigens by the antibody portion of the conjugate specific for the respective epitope, wherein by deactivation of the fluorochrome portion of the conjugate either according to the second embodiment by separation of the fluorochrome portion or according to the first embodiment by suppressing and extinguishing, respectively, the activity of the fluorochrome portion by a quencher, the site-specific binding of the binding portion is no longer detectable by detection of the fluorochrome portion. Therefore, in the detection method a further antibody conjugate can be contacted with the same sample subsequently in order to detect a further specific antigen, wherein the fluorochrome portion of the previously used antibody conjugate is inactive and therefore cannot produce disturbing emissions, for example no nonspecific emissions due to energy transfer, while the fluorochrome portion of the further antibody conjugate is detectable. In this embodiment, too, at least two antibody conjugates with different analyte specificity of the binding portion can be used in the place of one antibody conjugate.

Accordingly, the invention provides a detection conjugate and a method for its in-situ production, e.g. in contact with the sample, and the use of the detection conjugate for analysis. The detection conjugate has a binding portion and a fluorochrome portion as well as an oligonucleotide linker which preferably connects the binding portion and the fluorochrome portion to one another and which oligonucleotide linker can sectionally be single-stranded or double-stranded. The oligonucleotide linker in the second embodiment is hydrolysable by a nuclease and in the preferred first embodiment contains a quencher section. In a variant of the invention the section contained in the oligonucleotide linker to which section the oligonucleotide of the hybridizeable fluorochrome is hybridizeable and especially is reverse complementary, is also termed fluorochrome section. In the double-stranded embodiment the oligonucleotide linker in its nucleotide sequence has a fluorochrome section and the fluorochrome is connected to an oligonucleotide, which contains a section hybridizeable to the fluorochrome section, which section is e.g. reverse complementary. In the preferred embodiment the oligonucleotide linker has a quencher section and the detection conjugate is present in the combination in combination with a hybridizeable quencher which by contacting the detection conjugate deactivates its fluorochrome portion.

In an oligonucleotide linker which is sectionally double-stranded by hybridization of the hybridizeable fluorochrome to the fluorochrome section, the quencher section can be contained in that portion of the oligonucleotide linker which is connected to the fluorochrome as a second oligonucleotide linker section, e.g. directly and without nucleic acid hybridization, respectively, or in that section which is connected to the binding portion by nucleic acid hybridization. In this manner e.g. the second oligonucleotide linker section contains the quencher section which second oligonucleotide linker section is bound to the fluorochrome and is hybridizeable to the fluorochrome section. An oligonucleotide section which is connected without nucleic acid hybridization is connected e.g. covalently or by complex formation without participation of nucleic acids.

Preferably, the invention relates to an antibody conjugate to the quencher section of the oligonucleotide linker of which the oligonucleotide of a hybridizeable quencher is hybridized, and a method for its production by hybridization of the oligonucleotide of a hybridizeable quencher to the quencher section of the oligonucleotide linker, e.g. in the method for analysis. In the method according to the invention the antibody conjugate can be produced by contacting the sample with the components of the detection conjugate which preferably has an oligonucleotide linker having a quencher section, and preferably by subsequent contacting with a hybridizeable quencher. The contacting of the antibody conjugate with the hybridizeable quencher results in the deactivation of the fluorochrome portion and allows the subsequent analysis with a further detection conjugate having the same or a differing fluorochrome portion without occurrence of interactions with one of the detection conjugates used previously or concurrently, particularly for detection conjugates the quencher sections of which are unique each and specifically coordinated to a binding portion, respectively. The embodiments of the invention have the advantage that antibody conjugates with the same fluorochrome portion each can be used repeatedly in succession for the analysis of different antigens, i.e. with different antibody portions, since prior to contacting the sample with a further antibody conjugate fluorochrome portions which are already present in the sample have been deactivated each time. In detection conjugates of the invention the oligonucleotide linker, too, can have the same oligonucleotide sequence each time, since an interaction with oligonucleotide linkers or with oligonucleotides of hybridizeable quenchers of antibody conjugates which were contacted with the sample in previous steps of the detection method does not occur to a significant extent, especially not because of the washing steps, which are preferably carried out as a step of method after contacting with an antibody conjugate and/or after addition of a hybridizeable quencher and a nuclease, respectively.

Correspondingly, the method according to the invention in the first embodiment provides contacting a sample with the detection conjugate according to the invention, preferably washing for removal of unbound detection conjugate, irradiation of energy at an excitation wavelength in order to excite the fluorochrome portion for emission of radiation, detecting of emitted radiation, and subsequent deactivation of the fluorochrome portion by contacting with a hybridizeable quencher. Correspondingly, in the first embodiment the oligonucleotide linker has a quencher section.

In the second embodiment the deactivation of the fluorochrome portion occurs by hydrolyzing the oligonucleotide linker, for example by contacting with an endo-nuclease. After deactivation of the fluorochrome portion the sample is washed in order to remove unbound hybridizeable quencher and nuclease, respectively. Subsequently, the sample is contacted with a further detection conjugate according to the invention and its fluorochrome portion is detected, likewise by irradiation of an excitation wavelength and detection of emitted radiation. It has been found that the detection method is practicable for a sample of human cells which were immobilized on a microscope slide with at least 15 subsequent contacts with detection conjugates without considerable interaction of the detection conjugates between one another.

Oligonucleotide linkers and oligonucleotides bound to quenchers, particularly quencher sections and fluorochrome sections, preferably have differing unique nucleic acid sequences each, i.e. ones that have no sequence similarity to one another for hybridizing to other nucleic acids and that do not hybridize to the sample which is to be analyzed, particularly a nucleic acid sequence which is not hybridizeable and not complementary, respectively, to nucleic acids of cells which are to be analyzed. In embodiments in which the binding portion is an oligonucleotide the binding portion contains sequences complementary to the sample, whereas the oligonucleotide linker has a sequence which is not complementary to the sample and not hybridizeable therewith. Preferably, the oligonucleotide of the quencher has a sequence not complementary and not hybridizeable to the sample, but a sequence only hybridizeable to the quencher section of the oligonucleotide linker. The quencher is connected with its oligonucleotide such that upon hybridizing to the quencher section of the oligonucleotide linker it takes an arrangement in the immediate proximity of the fluorochrome portion.

In a variant of the invention which is possible in the first and second embodiment, the oligonucleotide of the linker which connects the binding portion to the fluorochrome portion is double-stranded in a section, in which an oligonucleotide linker section connected to the fluorochrome portion hybridizes to a section of the oligonucleotide linker which is connected to the binding portion. The second oligonucleotide linker section connected to the fluorochrome portion has a nucleotide sequence hybridizing to the fluorochrome section of the oligonucleotide linker, e.g. a reverse complementary nucleotide sequence. By hybridization of the second oligonucleotide linker section that is connected to the fluorochrome portion to the first oligonucleotide linker section connected to the binding portion, the conjugate has an oligonucleotide linker connecting the fluorochrome portion to the binding portion. Such a binding portion—oligonucleotide linker—fluorochrome portion conjugate has a sectionally double-stranded oligonucleotide linker by hybridization of the second oligonucleotide linker section connected to the fluorochrome portion.

According to the first embodiment, the oligonucleotide linker in a section is hybridizeable to the oligonucleotide of the quencher, e.g. in a quencher section of the first oligonucleotide linker section, to which the oligonucleotide connected to the quencher is hybridizeable. According to the second embodiment, the double-stranded section of the oligonucleotide linker, too, is hydrolysable, such that no additional single-stranded section within the oligonucleotide linker is necessary for the deactivation. For the second embodiment, the double-stranded section of the oligonucleotide linker can contain a recognition sequence for a restrictase. A fluorochrome provided with a second oligonucleotide linker section complementary to the first oligonucleotide linker section, which is also termed a hybridizeable fluorochrome, by the specific hybridization of its complementary second oligonucleotide linker section specifically connects to the fluorochrome section of the first oligonucleotide linker section bearing the binding portion and thereby forms the conjugate having a binding portion, an oligonucleotide linker having a section of a double-stranded nucleotide sequence, and a fluorochrome, or consisting of these elements. Correspondingly, the antibody-fluorochrome conjugate in this variant consists of at least a binding portion, at least a fluorochrome portion and at least a connecting sectionally double-stranded oligonucleotide linker and is therefore suitable for the specific deactivation of the fluorochrome portion, particularly by binding of a hybridizeable quencher having e.g. a reverse complementary nucleotide sequence to the quencher section of the oligonucleotide linker, or by hydrolysis of the oligonucleotide linker by means of a nuclease.

Also in the variant of the binding conjugates having an oligonucleotide linker which is sectionally double-stranded by hybridization of a second oligonucleotide linker section bound to the fluorochrome portion with the fluorochrome section, the binding conjugate can be formed when performing the method in admixture with the sample. Correspondingly, the test kit of the invention then comprises a first reagent having a first portion having a binding portion—first oligonucleotide linker section—conjugate, and separate from the first portion or in admixture with the first portion a second portion having a fluorochrome having a bound second oligonucleotide linker section hybridizeable with the fluorochrome section of the first oligonucleotide linker section.

In this variant the analytical method preferably comprises the steps of contacting a sample with the binding portion—oligonucleotide linker section—conjugate, washing the sample for removal of unbound binding portion—oligonucleotide linker section—conjugate, contacting the sample with a fluorochrome portion having an oligonucleotide section hybridizeable with the oligonucleotide linker section (also termed hybridizeable fluorochrome), and washing for removal of the unbound hybridizeable fluorochrome, and the optical detection of the fluorochrome. Subsequently, the fluorochrome portion is deactivated by contacting the sample with a quencher having an oligonucleotide hybridizeable with the oligonucleotide linker and/or by contacting with a nuclease with subsequent washing.

The fluorochrome section and the second oligonucleotide linker section of the hybridizeable fluorochrome hybridizeable therewith, as well as preferably the quencher section and the section of the oligonucleotide of the hybridizeable quencher hybridizeable therewith, are unique, particularly the fluorochrome section and the quencher section are preferably each unique and under the detection conditions exclusively form a double-stranded section with the sections of the oligonucleotides of hybridizeable fluorochrome and hybridizeable quencher, respectively, hybridizeable with them. Particularly preferred, the fluorochrome section and the quencher section are each unique and do not hybridize with each other under low stringent hybridizing conditions, e.g. under physiological conditions, in particular they are exclusively hybridizeable to the second oligonucleotide linker section of the hybridizeable fluorochrome and the oligonucleotide of the hybridizeable quencher, respectively, and particularly preferred they are not hybridizeable to a nucleotide sequence of the sample which is to be analyzed. In this manner, in the method according to the invention the formation of an oligonucleotide linker occurs in the fluorochrome section specific for the binding portion by hybridization to the second oligonucleotide linker section of the hybridizeable fluorochrome.

In this embodiment the quencher section is also then a component of the oligonucleotide linker, if it is a component of the second oligonucleotide linker section of the hybridizeable fluorochrome. This is because upon formation of the oligonucleotide linker by hybridization of its fluorochrome section to a section of the oligonucleotide of the hybridizeable fluorochrome that is reverse complementary and specific for the binding portion, the quencher section is a component of the oligonucleotide linker. The arrangement of the quencher section on the second oligonucleotide linker section of the hybridizeable fluorochrome is preferred here, because then in the method according to the invention upon contacting of a sample with a multitude of binding portions having an oligonucleotide linker having an unique fluorochrome section specific for the binding portion with subsequent contacting of the sample with only one hybridizeable fluorochrome each, the quencher section of the hybridizeable fluorochrome can be identical each time and correspondingly, the hybridizeable section of the oligonucleotide of the hybridizeable quencher each time can have the same unique nucleotide sequence that is reverse complementary to the quencher section.

It has been found that due to the specific deactivation of the fluorochrome portion the oligonucleotide linker of each embodiment of conjugates according to the invention, particularly of antibody conjugates according to the invention, is suitable in methods for analysis of living cells, particularly of animal cells and of tissue which can be in suspension as well as be immobilized on a substrate, for repeated successive contacting of the sample with detection conjugates.

Generally, the fluorochrome is arranged at a first end of the quencher section of the oligonucleotide linker and correspondingly, the quencher is connected to that end of its oligonucleotide which during hybridization is positioned adjacent to the first end of the quencher section. At the second end of the oligonucleotide linker opposite the first end of the quencher section the binding portion is arranged or the second end of the oligonucleotide linker is unconnected, if the binding portion is connected to the fluorochrome without an intermediate oligonucleotide linker.

If e.g. the first end of the oligonucleotide linker is the 3'-end of the quencher section, at which the fluorochrome portion is arranged, the quencher is preferably bound to the 5'-end of its oligonucleotide, and at its 3'-end, respectively, if the first end of the quencher section is the 5'-end of the oligonucleotide linker. Preferably, the oligonucleotide of the quencher is reverse complementary to the quencher section and the quencher is arranged at that end opposite the end of the nucleotide sequence of the quencher section, so that for an oligonucleotide of the quencher that is reverse complementary to the quencher section, the quencher is arrangeable in the proximity to the fluorochrome portion.

The basis for the analytical method according to the invention is the oligonucleotide linker each time which in the second embodiment allows the deactivation of a fluorochrome specific for the oligonucleotide linker by hydrolysis of the linker, and in the preferred first embodiment by the specific hybridization of an oligonucleotide bearing a quencher and having a quencher section.

Especially, the antibody conjugates according to the invention find a use in methods for analysis of biological samples which are in suspension or which are immobilized on a carrier and have denatured antigens, especially denatured and/or perforated prokaryotic and eukaryotic cells and tissue, especially animal cells and tissue.

In this manner, the conjugates according to the invention find use in the analysis of suspended analytes including cell-bound antigens, for example in flow cytometry for labelling of living animal cells, optionally with sorting of labelled cells in dependence from the detection of the fluorochrome.

In a preferred embodiment the analytical method according to the invention comprises the chronologically successive contacting of a biological sample immobilized on a carrier substrate, especially of living animal cells which are immobilized for example by binding to a coated carrier substrate, by a detection conjugate according to the invention. The immobilization on the carrier substrate which preferably is a microscopic object carrier of glass can for example be mediated by a coating of the carrier substrate promoting the adsorption of cells, e.g. a coating with polylysine. For the successive steps of contacting the biological sample with different aqueous compositions, the carrier substrate is preferably covered by a spaced lid, e.g. a cover glass arranged in parallel to the carrier substrate. For the spacing of the lid from the carrier substrate, the carrier substrate and/or the lid can have projections serving as spacers, for example two spaced projections arranged approximately in parallel to each other, which form a passage channel between them, the carrier substrate and the lid. The biological sample is immobilized and fixed, respectively, in the passage channel, namely on the carrier substrate, and can successively be contacted with compositions, wherein the identification of antibody conjugate interacting with an antigen of the sample is by detection of the radiation emitted by the fluorochrome portion which radiation is generated in response to irradiated irradiation having an excitation wavelength. Preferably, unbound detection conjugate is removed by exchange of the medium surrounding the sample subsequently to contacting the sample. The removal of unbound antibody conjugate preferably occurs by passing a flushing medium through the passage channel, such that only detection conjugate bound to the sample remains at the immobilized sample and emits radiation there, whereas unbound detection conjugate is removed from the sample by washing.

For immobilizing of biological samples, for example of tissue sections, a carrier substrate can be provided with a frame which is arranged on the carrier substrate as a projection having positive fit, for example having a height of 0.8-fold to 5-fold of the layer thickness of the tissue sample, preferably a height of 1-fold to 1.5-fold of the layer thickness of the tissue sample, wherein particularly preferred the lid is arranged at a distance to the tissue sample and the frame. In this manner, the frame on the carrier substrate arranged around a tissue sample with positive fit allows the passage of aqueous compositions through the passage channel which is formed between the carrier substrate and the lid, such that aqueous compositions, for example washing solutions and compositions containing the detection conjugate according to the invention, can flow towards and away from the fixed tissue sample.

Furthermore, biological samples, in particular animal cells and tissue samples can conventionally be denatured and/or perforated fixated on a carrier substrate.

Due to the immobilization and fixation, respectively, of the biological sample, the method for analysis according to the invention allows the superimposition of chronologically sequentially detected signals of different conjugates, especially of micrographs containing radiation emitted by the conjugates arranged at the sample. With particular advantage, the immobilization and the fixation of the biological sample in a passage channel allow to leave the sample in a determined position within the recording range of a detector, for example in the visual field of a microscope, or to repeatedly arrange the sample by identical arrangement of the carrier substrate within the recording range of the detector, for example within the visual field of a microscope, in the identical position each time during successive detection steps, for example with antibody conjugates having a different antibody portion each, e.g. when the detection steps of the contacting with different antibody conjugates are carried out in another position of the carrier substrate.

After antibody conjugate bound to the sample and its fluorochrome portion, respectively, have been detected optically, the fluorochrome portion can be deactivated and inactivated, respectively, according to the invention preferably by hydrolysis of the oligonucleotide linker or by contacting of the sample with a quencher which is connected to an oligonucleotide which in a section is reverse complementary to the oligonucleotide linker. Additionally or alternatively to the fluorochrome portion bound to the oligonucleotide linker a hybridizeable fluorochrome can be contacted with the antibody conjugate, resulting in specific hybridization of a fluorochrome to the antibody conjugate.

For the purposes of the invention, oligonucleotides and their sections are especially hybridizeable if they specifically form a dimer under cell physiological conditions, e.g. in a cell physiological buffer medium, preferably at 20 to 37° C. An oligonucleotide which is reverse complementary to a quencher section and to a fluorochrome section of the oligonucleotide linker, respectively, which oligonucleotide is connected to the quencher and the fluorochrome, respectively, especially describes an oligonucleotide which forms a double-stranded nucleic acid hybrid especially sequence-specifically with the oligonucleotide linker in the aqueous compositions used during the detection method, for example in PBS (phosphate buffered saline), HEPES buffer, Tris buffer, preferably at pH 6.5 to 7.5 at saline concentrations in the range of 20 to 800 mM of the sum of mono- and bivalent ions. These especially are oligonucleotides having a sequence reverse complementary to a section of the oligonucleotide linker, e.g. having an identity to the reverse complementary nucleic acid sequence of at least 80%, preferably of at least 90%, particularly preferably of at least 95 to 99%.

In variants, in which the oligonucleotide linker is double-stranded in a section in which an oligonucleotide linker section and an oligonucleotide section connected to the fluorochrome portion are hybridizeable and hybridized, respectively, the fluorochrome section and the second oligonucleotide linker section preferably have nucleic acid sequences that are reverse complementary to one another, which form a nucleic acid hybrid in the aqueous compositions used during the detection method, particularly having a reverse complementary sequence identity of at least 80%, preferably of at least 90%, particularly preferably of at least 95 to 99%.

The oligonucleotide linker and preferably the oligonucleotide bound to the quencher and the second oligonucleotide linker section of the fluorochrome, too, preferably have nucleic acid sequences not contained in the DNA and/or RNA of the sample which is to be analyzed, e.g. of the animal cell which is to be analyzed, the nucleic acid sequences especially having a sequence deviation of at least 5%, more preferably at least 10%, still more preferably at least 20%. Preferred lengths of the oligonucleotide linker, of the oligonucleotide bound to the quencher, and of the second oligonucleotide linker section of the fluorochrome range from 10 to 150 nt (nucleotides), preferably from 15 to 100 nt, more preferably from 20 to 50 nt of which at least 10, more preferably 30 nt, still more preferably all are complementary to one another.

A suitable fluorochrome can be selected from Cy3, PE, FITC, APC, Alexa dyes and atto dyes; a suitable quencher can be coordinated to the fluorochrome, e.g. from the group comprising Dabcyl, Dabsyl, dark-hole quenchers, black-berry quenchers and QSY dyes.

DETAILED DESCRIPTION OF THE INVENTION

Figure 2:
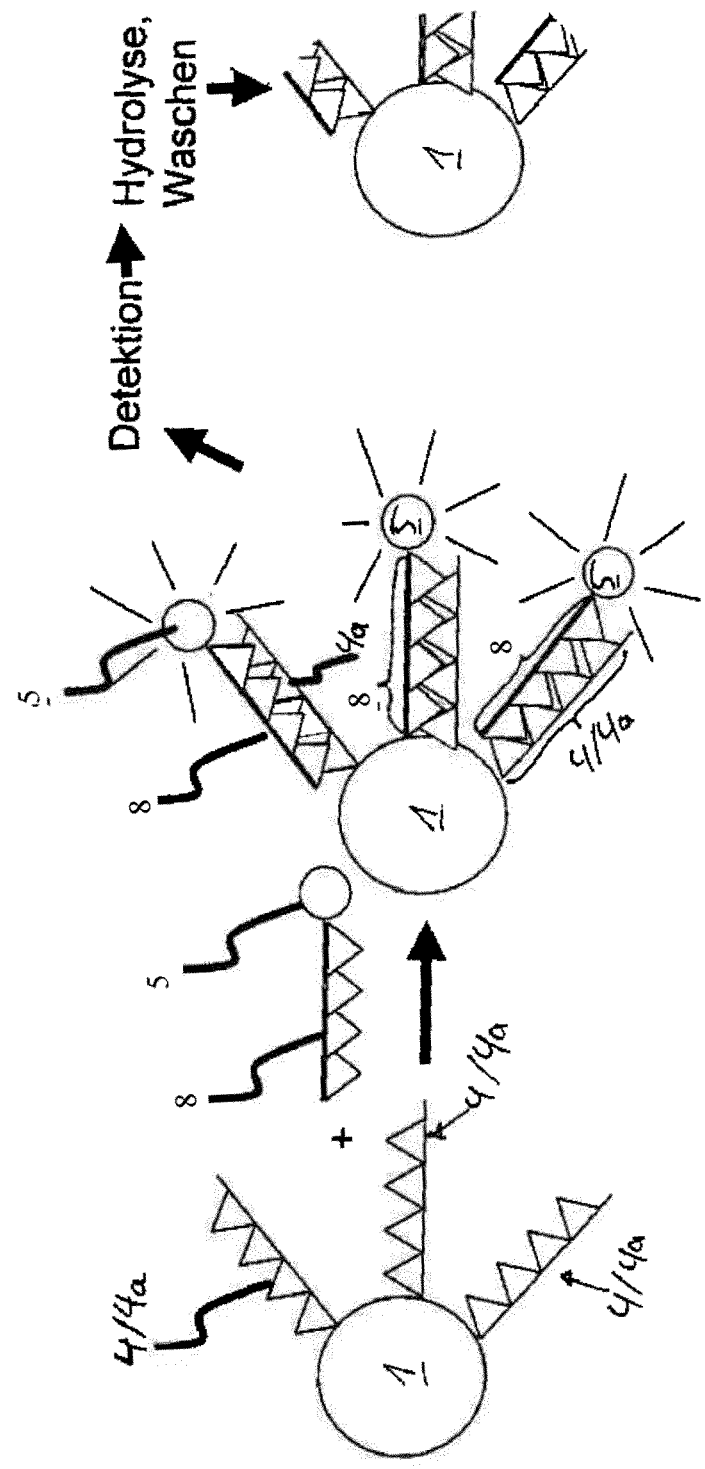
Figure 3:
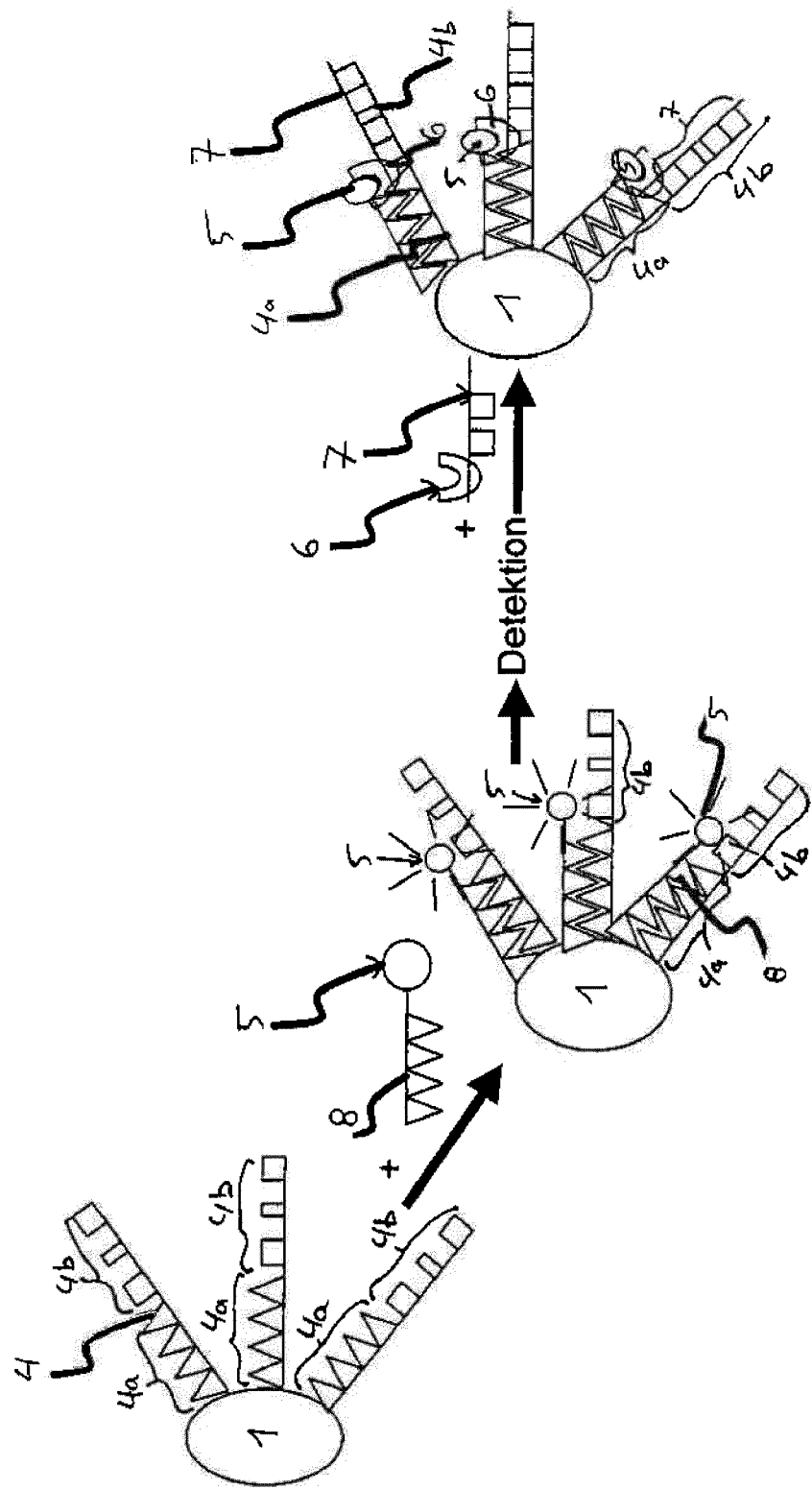
Figure 4:
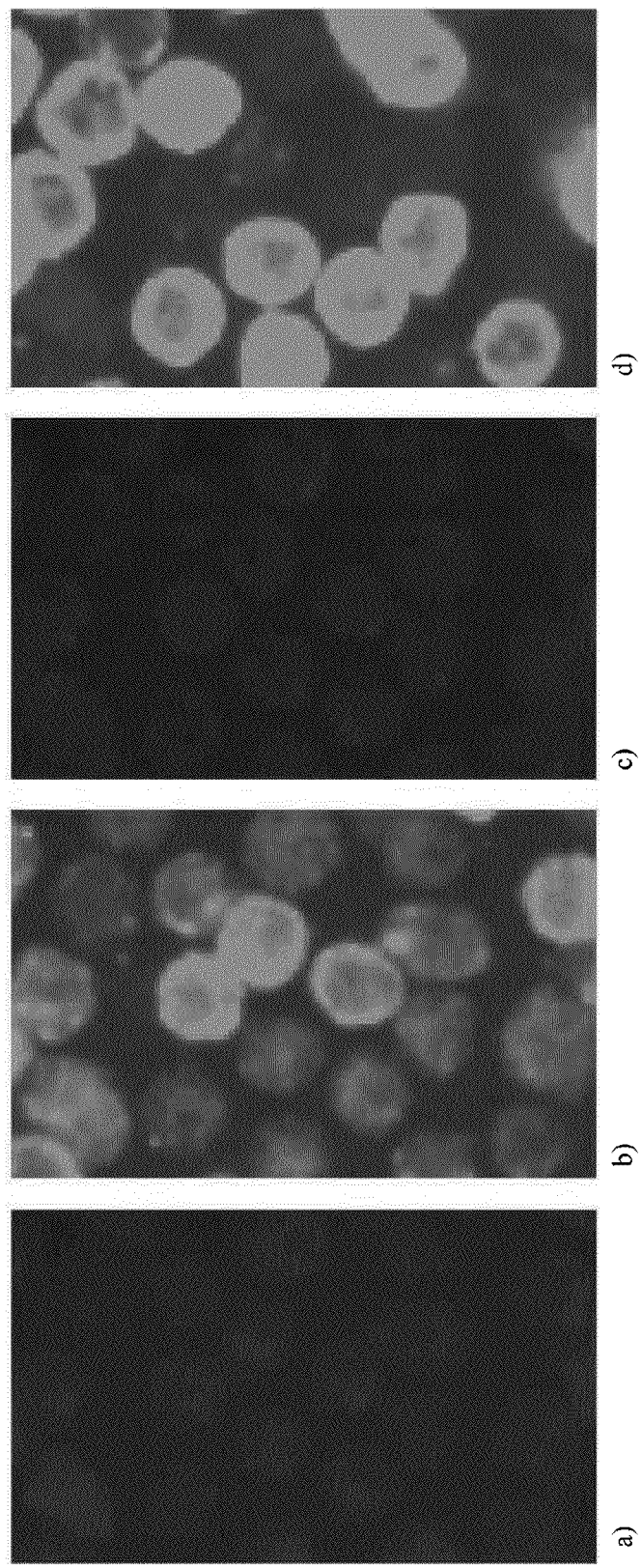

The invention will now be described in greater detail by way of examples with reference to the Figures, in which FIG. 1 shows a schematic depiction of the detection method of the first embodiment, FIG. 2 shows a schematic depiction of the detection method in a variant of the second embodiment, FIG. 3 shows a schematic depiction of the detection method of the first embodiment in a variant of the first embodiment, FIGS. 4 a) to d) immobilized human leukocytes after incubation with an antibody according to the invention in a micrograph upon excitation of the fluorescence in the steps of the detection method, FIGS. 5 a) to d) cell-free antigens immobilized from a solution after incubation with an antibody according to the invention in a micrograph upon excitation of the fluorescence in the steps of the detection method.

FIG. 6 shows micrographs A) of a biological sample with an antibody according to the invention and B) a micrograph of the same sample, but after hydrolysis of the antibody conjugate used under A) and incubation with a second antibody conjugate having a differing antigen specificity at the fixed sample, under C) FC results of the untreated cell sample, under D) FC results of an aliquot of the sample after incubation with an antibody according to the invention, and E) FC results of an aliquot of the sample analyzed under D) after hydrolysis of the linker.

FIG. 1 schematically shows the structure of a conjugate according to the invention in the first embodiment which as a first reagent of a test kit consists of the binding portion 1, the fluorochrome portion 5 and the oligonucleotide linker 4 connecting these. The fluorochrome portion 5, in this case Cy3, is covalently bound to the first end of the oligonucleotide linker 4, e.g. via bifunctional compounds. The binding portion 1 is schematically shown in the form of an IgG-antibody to which the second end of the oligonucleotide linker 4 is bound by means of a covalently bound first coupling reagent 2, e.g. streptavidin, and by means of a second coupling reagent 3, e.g. biotin, bound to the first coupling reagent 2. Upon irradiation of light (hv) having an excitation wavelength for the fluorochrome 5 radiation is emitted by the fluorochrome portion 5.

For binding of the second coupling reagent 3 the oligonucleotide linker 4 can terminally have a biotin-acceptor-domain (BAD). In the alternative to the binding of the oligonucleotide linker 4 to the binding portion 1 by means of a first and a second coupling reagent, the bond can be covalent, e.g. by derivatization of the binding portion 1 and/or of the oligonucleotide linker 4, e.g. for forming of an ester, amide or thio bond. The bond of the fluorochrome 5 to the oligonucleotide linker 4 preferably is covalent.

The oligonucleotide linker 4 can have the nucleic acid sequence TTT TTT TTT TGT TTT TTT TT (SEQ ID NO: 1) from 5' to 3', which as a quencher section 4b arranges the quencher 6 within the proximity of the fluorochrome portion 5 by contacting and hybridizing, respectively, with the oligonucleotide 7, which is connected to a quencher 6. Thereby, the fluorochrome portion 5 is optically deactivated. The oligonucleotide 7 that is hybridizeable to the quencher section 4b of the oligonucleotide linker 4 preferably is sectionally reverse complementary to the quencher section 4b, for example having the nucleic acid sequence AAA AAA AAA ACA AAA AAA AAA (SEQ ID NO: 2, from 5' to 3').

For positioning the quencher 6 in the proximity of the fluorochrome 5, especially within the Förster radius, the quencher 6 is preferably bound to that end of the oligonucleotide 7, which is adjacent to the fluorochrome 5 upon forming of a hybrid with the oligonucleotide linker 4.

For the analytical method a sample can be contacted with the first reagent consisting of a binding portion 1, fluorochrome portion 5 and the oligonucleotide linker 4 bound by its first end to the fluorochrome portion 5. After washing the specific binding of the binding portion 1 to the sample can be analyzed by detection of the fluorochrome portion. The oligonucleotide linker 4 has a quencher section 4b to which an oligonucleotide 7 connected to the quencher 5 is hybridizeable. By contacting the first reagent which is bound to the sample, with a second reagent having a quencher 6 bound to an oligonucleotide 7, the fluorochrome portion 5 is deactivated. The subsequent contacting of the sample with a further first reagent allows the detection of its fluorochrome portion without impairment by the first reagent previously contacted with the sample, the fluorochrome of which first reagent has been deactivated by arrangement of the quencher 6 in its proximity. In the alternative to the deactivation by specific arrangement of a quencher 6 at the first reagent, its fluorochrome portion 5 can be deactivated effectively by hydrolysis of the oligonucleotide linker 4 and washing, as schematically depicted for the second embodiment in FIG. 2.

FIG. 2 schematically shows the structure of a conjugate according to the invention of the second embodiment consisting of a binding portion 1, in this case shown as a receptor ligand, and a fluorochrome 5 bound thereto by means of an oligonucleotide linker 4 covalently bound to the binding portion 1. The oligonucleotide linker 4 is double-stranded in the section in which the second oligonucleotide linker section 8 bound to the fluorochrome 5 is hybridized with the hybridizeable first oligonucleotide linker section 4a. Preferably, the bonds between the binding portion 1 and the first oligonucleotide linker section 4a, as well as those between the second oligonucleotide linker section 8 and the fluorochrome 5 have been formed by association of first and second coupling reagents each bound covalently to one component according to FIG. 1, or covalently.

Since the second embodiment also in this variant of the sectionally double-stranded oligonucleotide linker 4 has an oligonucleotide linker 4 that is hydrolysable by an endonuclease, herein an endonuclease is contained in the test kit as second reagent. Correspondingly, herein the oligonucleotide linker 4 optionally has no quencher section 4b.

In the analytical method the sample can be contacted with a first portion of the first reagent consisting of a binding portion with a bound oligonucleotide linker 4 having a first oligonucleotide linker section 4a containing a fluorochrome section, and simultaneously or subsequently can be contacted with a second portion containing the fluorochrome portion 5 bound to the second oligonucleotide linker section 8 which is hybridizeable or hybridized to the first oligonucleotide linker section 4a. After removal of unbound portions from the sample by washing, specifically bound binding portion 1 can be identified by detection of the fluorochrome portion 5 bound thereto via the sectionally double-stranded oligonucleotide linker 4. For deactivation of the fluorochrome portion 5 the oligonucleotide linker 4 can be removed and thereby be effectively deactivated from the binding portion 1 by contacting with an endonuclease (not depicted) and subsequent washing.

FIG. 3 schematically shows the structure of a conjugate according to the invention in the first embodiment in the variant in which the oligonucleotide linker 4 is sectionally double-stranded. The binding portion 1 is bound to the oligonucleotide linker 4 which has a first oligonucleotide linker section 4a having a fluorochrome section to which the second oligonucleotide linker section 8 bound to the fluorochrome portion 5 is hybridizeable. Correspondingly, the oligonucleotide linker 4 has the first oligonucleotide linker section 4a to which the second oligonucleotide linker section 8, to which the fluorochrome 5 is bound, is sectionally hybridizeable, e.g. is reverse complementary. The oligonucleotide linker 4 has a quencher section 4b adjacent to the first oligonucleotide section 4a to which quencher section 4b the oligonucleotide 7 bound to the quencher 6 is hybridizeable, e.g. reverse complementary. For positioning the fluorochrome 5 in the vicinity of the quencher 6 the fluorochrome 5 preferably is bound to that end of the second oligonucleotide linker section 8 which upon hybridization with the first oligonucleotide linker section 4a borders on the quencher section 4b of the oligonucleotide linker 4, with which the oligonucleotide 7 bearing the quencher 6 is hybridized. For positioning the quencher 6 in the proximity of the fluorochrome 5, especially within the Förster radius, the quencher 6 preferably is bound to that end of the oligonucleotide 7 which upon forming of a hybrid with the oligonucleotide linker 4 and its quencher section 4b, respectively, borders on the first oligonucleotide linker section 4a of the oligonucleotide linker 4, to which the second oligonucleotide linker section 8 of the fluorochrome 5 is hybridizeable.

Upon hybridization of the second oligonucleotide linker section 8 connected to the fluorochrome 5 with the first oligonucleotide linker section 4 the binding portion 1 is connected to the fluorochrome 5, such that upon irradiation of light by having excitation wavelength fluorescence is emitted. This emission is measured for detection of the conjugate according to the invention.

The addition of hybridizeable quencher 6 which is connected to an oligonucleotide 7 that is complementary to a quencher section 4b of the oligonucleotide linker 4 by positioning of the quencher 6 in the proximity to the fluorochrome 5 results in the deactivation of the fluorochrome 5.

As shown in FIGS. 1 to 3, the conjugates according to the invention can have one or more oligonucleotide linkers 4 bound to the binding portion 1.

Example 1

Production of an Antibody-Fluorochrome Conjugate Having an Oligonucleotide Linker As an example for the conjugate of the first embodiment according to the invention a biotinylated anti-Mouse-CD4 antibody (clone GK1.5, obtainable from BD Bioscience) was incubated with streptavidin and the streptavidin-antibody conjugate that was formed was purified. As an oligonucleotide linker, synthetically produced single-stranded DNA of SEQ ID NO: 1 was used, to the 3'-end of which biotin was coupled and to the 5'-end of which the fluorophore Cy3 (obtainable from Molecular Probes Inc.) was coupled. For binding the oligonucleotide linker to the antibody used as a binding portion, the biotinylated oligonucleotide was incubated with the streptavidin-coupled antibody and was subsequently purified by gel chromatography. The bond between streptavidin and biotin resulted in a conjugate of the structure antibody-biotin-streptavidin-biotin-oligonucleotide linker-fluorochrome.

Example 2

Detection of an Antigen on the Cell-Surface of Human Cells

As an example for a biological sample human leucocytes were isolated from peripheral blood and immobilized on a microscope slide of glass having a cell-adhesive coating (polylysine, obtainable from Karl Roth GmbH). For spacers, the microscope slide had two projections spaced in parallel, which bore a cover glass in parallel to the microscope slide. The openings formed at each end of the microscope slide were used as inlet opening and outlet opening, respectively, for introduction and removal of solutions.

After removal of unbound components by washing with physiological phosphate buffered saline (PBS, pH 7.4), the cells were analyzed microscopically (axioplan 2e microscope, Zeiss, with motorized object stage adjustment and focussing, mercury lamp HBO 100 for excitation, filter for PE or FITC, Plan-Neofluar 16x/0.5 immersion objective, and CCD camera Axiocam MRm for recording) upon irradiation of an excitation wavelength in order to determine the background fluorescence. The micrograph obtained is shown in FIG. 4 a) in which lightmicroscopically identified cells are labelled by inserted circles. Subsequently, antibody conjugate containing anti-CD4 antibodies as antibody portion according to Example 1 was added. FIG. 4 b) shows the same site as FIG. 4 a) at fluorescence detection of the light emitted by the fluorochrome Cy3. This image shows that conjugates according to the invention are suitable for the specific detection of cell antigens, since the CD4-positive cells are labelled selectively.

Subsequently an oligonucleotide connected to a quencher was added to the cells through the inlet opening, namely the oligonucleotide SEQ ID NO: 2 which is sectionally reverse complementary to SEQ ID NO: 1, to the 3' end of which oligonucleotide the quencher BHQ 2 (black-hole quencher, obtainable from BioSearch, Novato, USA) was bound. After incubation for 1 min at room temperature 100 µL PBS were added for washing at the inlet opening and approximately the same volume was removed from the outlet opening. A renewed fluorescence micrograph of the same site is shown in FIG. 4 c). This result makes it clear that the optical activity of the fluorochrome of the conjugate according to the invention can be deactivated selectively. In the alternative to the addition of the quencher bearing the oligonucleotide, DNase could be added for the deactivation of the fluorochrome portion, followed by washing with approximately 100 to 200 µL PBS in order to hydrolyze the oligonucleotide linker of the conjugate and to remove the fluorochrome.

Subsequently the same immobilized cells were contacted with an antibody conjugate produced according to Example 1, but having an anti-mouse-CD19 antibody. The fluorescence micrograph is shown in FIG. 4 d), which makes it clear that conjugates according to the invention are suitable for successive detection of antigens, each time with specific deactivation of the fluorochrome portion of a conjugate prior to contacting of the sample with a further conjugate. The fluorescence of the anti-CD19 conjugate, too, could be deactivated, i.e. could be removed, by addition of the same quencher bearing the oligonucleotide reverse complementary to the oligonucleotide linker, or by addition of DNase.

Example 3

Successive Detection of Soluble Antigens after Immobilization on a Carrier Substrate Conjugates according to the invention were used for analysis of cell-free analytes, for example for detection of surface-bound IgG2a. Phycoerythrin-labelled rat immunoglobulin Ig2Ga kappa was allowed to bind to a microscope slide of glass coated with polylysine as used in Example 2. Subsequently, free binding positions of the microscope slide were saturated with bovine serum albumin (3% in PBS). A fluorescence micrograph is shown in FIG. 5 a), in which the fluorescence of single molecules is visible. The position of the labelled IgG2a was determined and stored in relation to the microscope slide.

For extinguishing of the autofluorescence of the phycoerythrin-labelled rat immunoglobulin irradiation with the specific excitation wavelength (488 nm) was used. The single molecule micrograph and the fluorescence micrograph in FIG. 5 b) shows that the fluorescence activity of the phycoerythrin was thereby extinguished.

Subsequently an antibody conjugate produced according to Example 1 but having an anti-IgG2a antibody was added. Unbound conjugate was removed by washing with PBS. The subsequent fluorescence micrograph of FIG. 5 c) shows that the same positions were labelled by the conjugate according to the invention as in FIG. 5 a), and therefore these conjugates are also suitable for the identification of cell-free analytes.

Using subsequent incubation with the quencher of Example 2 connected to a reverse complementary oligonucleotide resulted in the deactivation of the fluorescence of the conjugate according to the invention specific for the analyte. A fluorescence micrograph is shown in FIG. 5 d), from which the extinction of the fluorescence of the conjugates is evident. In the alternative to the quencher, DNase could be added and the immobilized analytes could be washed in order to deactivate the fluorescence of the conjugate.

Example 4

Hydrolysis of an Antibody Conjugate According to the Invention at Immobilized Human Cells and at Suspended Human Cells (FC)

It could be shown that the fluorochrome portion of an antibody conjugate according to the invention which is obtainable according to Example 1 and the antibody portion of which was an anti-CD4 antibody and the fluorochrome portion of which was Cy3, which were connected by an oligonucleotide linker (SEQ ID NO: 1), could be deactivated on living immobilized immune cells and on suspended living immune cells.

In accordance with Example 2, immobilized human immune cells were incubated with the antibody conjugate; the micrograph including the detected fluorescence is shown in FIG. 6 A). Subsequently, the sample was treated by contacting with DNase in order to separate the fluorochrome portion. For removal of unbound fluorochrome the immobilized sample was washed. Alternatively, the hybridizeable quencher used in Example 1 having a reverse complementary oligonucleotide to the quencher section of the oligonucleotide linker was added, which also resulted in the deactivation of the fluorochrome.

Figure 5:
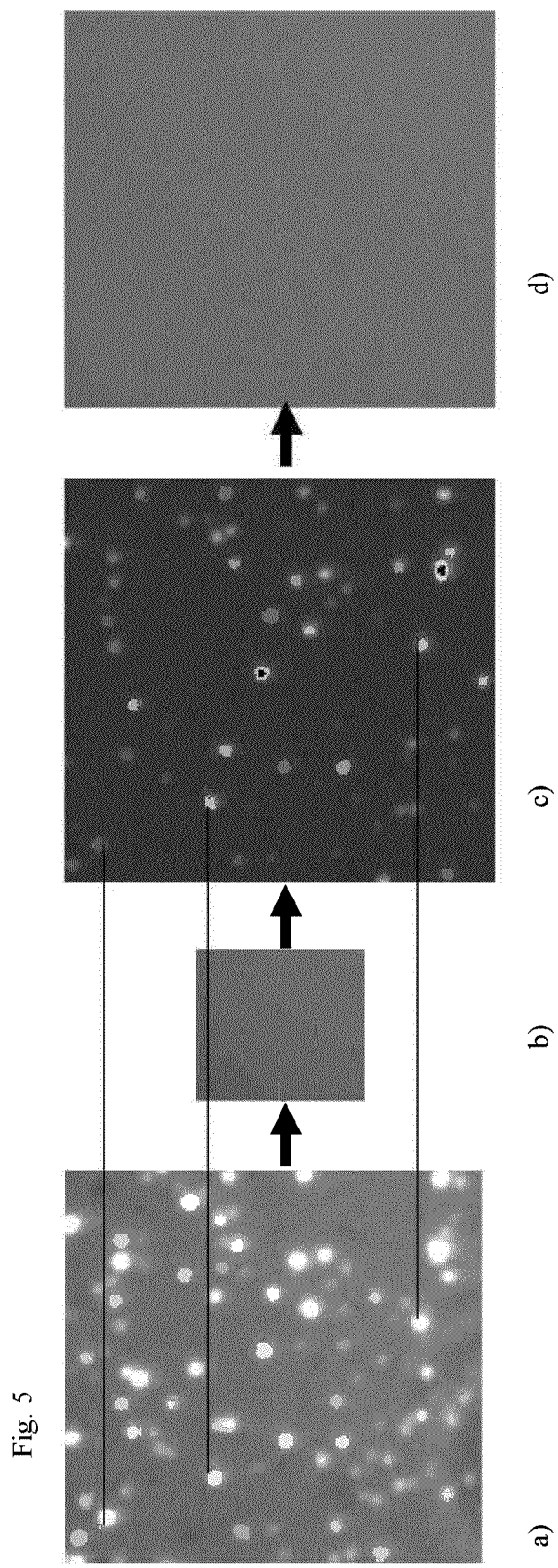

Subsequently, the sample was incubated with an antibody conjugate having the same oligonucleotide linker, but having an anti-CD19 antibody portion and PE as the fluorochrome portion; the micrograph of detected emissions is shown in FIG. 5 b) and makes it evident that the cells detected with the anti-CD4 antibody conjugate (each marked by manually inserted circles) did not produce a fluorescence signal in the analysis with anti-CD19 antibody conjugate.

As a proof for the effective deactivation of the fluorochrome portion of an antibody conjugate by separating of the fluorochrome portion, an aliquot of cells without antibody conjugate, an aliquot of the cells after incubation with antibody conjugate (anti-CD4 antibody-oligonucleotide linker-Cy3), and an aliquot therefrom after hydrolysis of the linker by incubation with DNase were analyzed by FC. The results are shown in FIG. 7C) for cells not incubated with antibody conjugate, D) for cells incubated with anti-CD4-antibody conjugate and E) of cells incubated with anti-CD4 antibody conjugate after hydrolysis of the linker. The FC analyses make it clear that the antibody conjugate according to the invention could effectively identify the surface marker and that antibody conjugate bound to the cells generates a detectable signal of emitted radiation, wherein the hydrolysis of the oligonucleotide linker with subsequent washing resulted in the complete deactivation of the fluorochrome portion. Corresponding results were also obtained by addition of the hybridizeable quencher having an oligonucleotide that is reverse complementary to the quencher section of the oligonucleotide linker.

Example 5

Use of the Conjugates for Iterative Cell Sorting by FC

Spleen cells of the mouse in suspension in PBS were incubated with an anti-CD3 antibody conjugate produced according to Example 1 for 10 min at room temperature. Fluorescence-labelled cells, in this case T-helper lymphocytes, are separated from the remaining cells by flow cytometry (FACXAria, BD Biosciences). The T-helper lymphocytes are then incubated in PBS with the quencher having an oligonucleotide used in Example 2 for 10 min at room temperature. The subsequent analysis by FC showed that the fluorochrome was deactivated. After separation of the quencher the T-helper lymphocytes could be analyzed and sorted with a second antibody conjugate having a differing antibody portion but the same oligonucleotide linker and the same fluorochrome.

LIST OF REFERENCE NUMERALS 1 binding portion
2 first coupling reagent
3 second coupling reagent
4 oligonucleotide linker
4a fluorochrome section
4b quencher section
5 fluorochrome
6 quencher
7 oligonucleotide reverse complementary to the quencher section 4b of the oligonucleotide linker 4
8 second oligonucleotide linker section hybridizeable with the fluorochrome section of the oligonucleotide linker

The invention claimed is:

1. A detection conjugate for detection of analytes in samples, comprising
a first reagent having a detection conjugate having a binding portion specific for an analyte, a fluorochrome portion connected to the binding portion, and an oligonucleotide linker connected by its first end to the fluorochrome portion, which oligonucleotide linker at least in a section is an oligonucleotide having a quencher section within its nucleic acid sequence, and
a second reagent having a quencher that is connected to that end of an oligonucleotide hybridizeable to the quencher section which upon hybridizing with the oligonucleotide linker is located at the first end thereof,
wherein the binding portion is selected from the group consisting of antibodies, antibody fragments forming a paratope, lectins, peptides specific for predetermined MHC I, peptides specific for predetermined MHC II, and MHC tetrameres.

2. The detection conjugate according to claim 1, wherein the oligonucleotide linker is connected to the binding portion with its second end opposite the first end.

3. The detection conjugate according to claim 1, wherein the oligonucleotide linker has a first oligonucleotide linker section that is bound to the binding portion, wherein the first oligonucleotide linker section in its nucleic acid sequence has a fluorochrome section, and in that the fluorochrome portion is connected to a second oligonucleotide linker section hybridizeable to the fluorochrome section.

4. The detection conjugate according to claim 3, wherein the second oligonucleotide linker section that is connected to the fluorochrome portion has the quencher section.

5. The detection conjugate according to claim 4, wherein at least two detection conjugates are contained, each having fluorochrome sections with identical or similar nucleotide sequences to which the same second oligonucleotide linker section is hybridizeable under physiological conditions.

6. The detection conjugate according to claim 1, wherein at least two detection conjugates are contained, each having quencher sections of unique nucleotide sequences.

7. The detection conjugate according to claim 1, wherein at least two detection conjugates are contained, each having quencher sections having identical or similar nucleotide sequences to which the same oligonucleotide connected to the quencher is hybridizeable under physiological conditions.

8. A detection conjugate for detection of analytes in samples, comprising
a first reagent having a detection conjugate having a binding portion specific for an analyte, a fluorochrome portion connected to the binding portion, and an oligonucleotide linker connected by its first end to the fluorochrome portion, which oligonucleotide linker at least in a section is an oligonucleotide having a quencher section within its nucleic acid sequence, and
a second reagent which is a nuclease,
wherein the binding portion is selected from the group consisting of antibodies, antibody fragments forming a paratope, lectins, peptides specific for predetermined MHC I, peptides specific for predetermined MHC II, and MHC tetrameres.

9. The detection conjugate according to claim 8, wherein the oligonucleotide linker has a recognition sequence for a restrictase and the nuclease is a restrictase specific for the recognition sequence.

10. The detection conjugate according to claim 1, wherein independent from one another, the oligonucleotide linker and/or the oligonucleotide connected to the quencher is a single-stranded oligo ribonucleic acid (RNA), oligo deoxyribonucleic acid (DNA), or oligo peptidenucleic acid (PNA).

11. The detection conjugate according to claim 3, wherein independent from one another, the first oligonucleotide linker section of the oligonucleotide linker and/or the second oligonucleotide linker section hybridizeable thereto which is connected to the fluorochrome portion, is a single-stranded oligo ribonucleic acid (RNA), oligo deoxyribonucleic acid (DNA), or oligo peptidenucleic acid (PNA).

12. The detection conjugate according to claim 1, wherein two or more oligonucleotide linkers are connected to the binding portion.

13. A method for analysis of a biological sample with the detection conjugate according to claim 1, comprising:
contacting the sample with the first reagent having a detection conjugate having a binding portion specific for a first analyte, contacting the sample with the second reagent, and contacting the sample with a detection conjugate having a binding portion specific for a second analyte.

14. A method for analysis of biological samples, comprising the production of the detection conjugate according to claim 1 in contact with the sample.

15. A method for analysis of biological samples, comprising the steps of:
contacting a biological sample with a detection conjugate having a binding portion having a first specificity for a first analyte, a fluorochrome portion connected to the binding portion, and a linker connected by its first end to the fluorochrome portion,
detecting radiation emitted by the fluorochrome portion, and
deactivating the fluorochrome portion,
wherein
the linker is an oligonucleotide linker which at least in a section is an oligonucleotide having in its nucleic acid sequence a quencher section, and wherein
the deactivation of the fluorochrome portion occurs by contacting the detection conjugate with a quencher which is connected to that end of an oligonucleotide hybridizeable with the quencher section which upon hybridizing to the oligonucleotide linker is located at the first end thereof,
wherein the binding portion is selected from the group consisting of antibodies, antibody fragments forming a paratope, lectins, peptides specific for predetermined MHC I, peptides specific for predetermined MHC II and MHC tetrameres.

16. The method according to claim 15, comprising the subsequent contacting of the sample with a detection conjugate of a first analyte specificity, contacting of the sample with a quencher specific for the first detection conjugate, and contacting of the sample with a detection conjugate of a second analyte specificity.

17. The method according to claim 16, wherein the fluorochrome portion and the oligonucleotide linker of detection conjugates used in subsequent contactings are identical to each other and each time the quencher is the same having the same oligonucleotide.

18. A method for analysis of biological samples, wherein deactivating the fluorochrome portion occurs by contacting the detection conjugate with a nuclease and subsequent removal of unbound components, the method comprising the steps of:
- contacting a biological sample with a detection conjugate having a binding portion having a first specificity for a first analyte, a fluorochrome portion connected to the binding portion, and a linker connected by its first end to the fluorochrome portion,
- detecting radiation emitted by the fluorochrome portion,
- deactivating the fluorochrome portion, wherein
- the linker is an oligonucleotide linker, and
- deactivating the fluorochrome portion occurs by contacting the detection conjugate with a second reagent which is a nuclease,
- wherein the binding portion is selected from the group consisting of antibodies, antibody fragments forming a paratope, lectins, peptides specific for predetermined MHC I, peptides specific for predetermined MHC II, and MHC tetrameres.

19. The method according to claim 15, wherein the oligonucleotide linker has a first oligonucleotide linker section which is bound to the binding portion and in its nucleotide sequence has a fluorochrome section, and in that the binding conjugate is produced by contacting the fluorochrome section with a fluorochrome portion which is connected to a second oligonucleotide linker section hybridizeable to the fluorochrome section.

20. The method according to claim 19, wherein the sample is simultaneously contacted with at least two detection conjugates, the fluorochrome sections of which are each unique.

21. The method according to claim 15, wherein the sample is simultaneously contacted with at least two detection conjugates, the quencher sections of which are each unique.

22. The method according to claim 15, wherein the analytes are fixed on a carrier substrate.

23. The method according to claim 22, wherein the carrier substrate is part of a flow channel, in which the analytes are arranged for being circumfused by aqueous compositions.

24. The detection conjugate according to claim 8, wherein the oligonucleotide linker has no quencher section.

25. The detection conjugate according to claim 15, wherein the oligonucleotide linker has a first oligonucleotide linker section that is bound to the binding portion, wherein the first oligonucleotide linker section in its nucleic acid sequence has a fluorochrome section, and in that the fluorochrome portion is connected to a second oligonucleotide linker section hybridizeable to the fluorochrome section.

26. The method according to claim 18, wherein the oligonucleotide linker has a recognition sequence for a restrictase and the nuclease is a restrictase specific for the recognition sequence.

27. The method according to claim 19, comprising the subsequent contacting of the sample with a detection conjugate of a first analyte specificity, contacting of the sample with a quencher specific for the first detection conjugate, and contacting of the sample with a detection conjugate of a second analyte specificity.

28. The method according to claim 18, wherein the analytes are fixed on a carrier substrate.

29. The method according to claim 18, wherein the carrier substrate is part of a flow channel, in which the analytes are arranged for being circumfused by aqueous compositions.

* * * * *